United States Patent [19]

Tang et al.

[11] Patent Number: 4,584,142
[45] Date of Patent: Apr. 22, 1986

[54] ALKYL PERCARBONATES

[75] Inventors: Robert H. Tang, Norton; James A. Barter, Akron, both of Ohio

[73] Assignee: PPG Industries, Inc., Pittsburgh, Pa.

[21] Appl. No.: 548,373

[22] Filed: Nov. 3, 1983

[51] Int. Cl.$^4$ ........................................... C07C 179/15
[52] U.S. Cl. .................................... 558/264; 558/280; 526/230.5
[58] Field of Search ......................... 260/453 RZ, 463

[56] References Cited

U.S. PATENT DOCUMENTS

| Re. 25,763 | 4/1965 | Marous et al. | 260/92.8 |
|---|---|---|---|
| 2,370,588 | 2/1945 | Strain | 260/453 |
| 2,843,576 | 7/1958 | Dunn et al. | 260/92.3 |
| 3,720,700 | 3/1973 | Norback | 260/463 |
| 3,799,966 | 3/1974 | Sanchez | 260/463 |
| 4,137,252 | 1/1979 | Komai et al. | 260/463 |

OTHER PUBLICATIONS

Esters of Peroxycarbonic Acids, F. Strain et al., J. A. Chem. Soc. vol. 72, pp. 1254–1263, (1950).
Use of Mixed Carboxylic—Carbonic Anhydrides for Acylations on Carbon and Oxygen, D. Tarbell et al., J. Org. Chem. vol. 22, pp. 245–250, (1957).

Primary Examiner—Henry R. Jiles
Assistant Examiner—Robert C. Whittenbaugh
Attorney, Agent, or Firm—Irwin M. Stein

[57] ABSTRACT

Organic peroxydicarbonates represented by the following graphic formula are described.

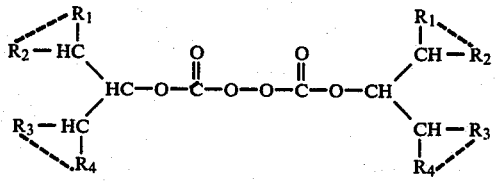

In the formula, $R_1$, $R_2$, $R_3$ and $R_4$ are each independently selected from an alkyl group containing from 1 to 4 carbon atoms. $R_1$ and $R_2$ and/or $R_3$ and $R_4$ can participate in a cycloalkyl group having from 3 to 6 carbon atoms. The peroxydicarbonates are useful as initiators for the polymerization or copolymerization of ethylenically unsaturated monomers or the cross-linking of unsaturated polyester resins. The organic peroxydicarbonates can be used in combination with commercially available peroxydicarbonates, particularly those having a longer half-life, or with peresters, diacylperoxides and azo compounds.

3 Claims, No Drawings

ALKYL PERCARBONATES

DESCRIPTION OF THE INVENTION

The present invention relates to certain novel peroxydicarbonates and to their use in the polymerization and copolymerization of ethylenically unsaturated monomers, e.g., vinyl chloride. The utility of certain peroxydicarbonate compounds for initiating polymerization reactions is known. See, for example, U.S. Pat. No. 2,370,588 and J. A. Chem. Soc., 72, 1254 (1950), which disclose the preparation of various dialkyl peroxydicarbonates and their use as polymerization initiators. See also, Dunn et al, U.S. Pat. No. 2,843,576 and Marous et al, U.S. Pat. No. Re. 25,763.

Dialkyl peroxydicarbonates are generally used as low temperature free-radical polymerization initiators. The stability of such dialkyl peroxydicarbonates at room temperature, i.e., the shelf life at room temperature, is not as long as less reactive peroxides because of their activity at relatively low temperatures. Consequently, dialkyl peroxydicarbonates such as diisopropyl-, di-n-propyl- and di-secondary butyl peroxydicarbonates are shipped under refrigeration. While the use of such peroxydicarbonates requires special handling techniques for shipment and storage, i.e., refrigeration, their use is preferred for many polymerizations for the reasons that they are more efficient at the polymerization temperatures utilized than the less reactive organic peroxides, such as lauroyl peroxide and dibenzoyl peroxide, and result in lower levels of residual peroxide in the polymer product. Consequently use of these peroxydicarbonates results in shorter polymerization times per batch of polymer produced and less polymer degradation due to residual peroxide.

Attempts have been made to reduce the rate of self-induced homolytic decomposition of dialkyl peroxydicarbonates, i.e., improve their shelf life under non-refrigerative storage conditions, by increasing the size of the organic radical at the terminal ends of the peroxydicarbonate molecule. For example, U.S. Pat. No. 3,720,700 describes the chemical compound, dicetyl peroxydicarbonate, which is reported to have superior storage stability compared with peroxydicarbonates such as diisopropyl peroxydicarbonate. U.S. Pat. No. 4,137,252 describes dicyclododecyl peroxydicarbonate as being stable at room temperature and as losing only 6.6 percent of its assay when stored for three weeks at a temperature of 30° C. U.S. Pat. No. 3,799,966 describes di(2-phenoxyethyl)peroxydicarbonate as being stable at 50° C. with little or no loss of assay.

While the aforesaid high molecular weight peroxydicarbonates are reported to be more stable at room temperature than the more common normally liquid, i.e., liquid at room temperature (20° C.), peroxydicarbonates, they possess a low percent active oxygen (per unit molecular weight) relative to the normally liquid peroxydicarbonates because of their higher molecular weight. For example, dicetyl peroxydicarbonate has a value of 2.8% active oxygen; whereas disecondarybutyl peroxydicarbonate has a value of 6.8% active oxygen. There is, therefore, a continuing need for peroxydicarbonates which have improved storage stability at room temperature relative to the normally liquid peroxydicarbonates, are efficient at the polymerization temperatures at which the normally liquid peroxydicarbonates are used, and which possess a relatively high percent active oxygen.

It has now been discovered that organic peroxydicarbonates represented by the following graphic formula I possess the desirable properties of improved shelf life at room temperature, good efficiency at low polymerization temperatures and a relatively high percent active oxygen.

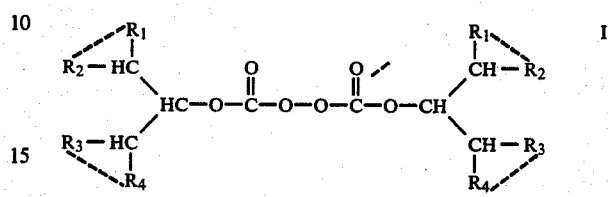

In graphic formula I, R, $R_1$, $R_2$, $R_3$ and $R_4$ are each an alkyl group containing from 1 to 4 carbon atoms, provided, however that not more than one of $R_1$ or $R_2$, and not more than one of $R_3$ or $R_4$ is tertiary butyl. In addition, $R_1$ and $R_2$ and/or $R_3$ and $R_4$ can participate in a cycloalkyl group having from 3 to 6 carbon atoms (as shown by the broken lines connecting $R_1$ and $R_2$ and $R_3$ and $R_4$). The aforesaid described peroxydicarbonates are solids at room temperature and consequently can be stored at such temperature for short periods of time, e.g., less than 30 days without refrigeration. However, from the evidence at hand, it is possible for these peroxydicarbonates to undergo homolytic decomposition if allowed to remain at room temperature for extended periods. Therefore, at the present time, it is recommended that storage temperatures less than room temperature be employed.

Further, it has been found surprising that the half-life of such peroxydicarbonates at 50° C. (as measured in trichloroethylene) is significantly shorter than the corresponding half-life of the common normally liquid dialkyl peroxydicarbonates, such as disecondarybutyl peroxydicarbonate and di(2-ethylhexyl)peroxydicarbonate. For example, the compound di(2,4-dimethyl-3-pentyl)peroxydicarbonate has a half life at 50° C. (measured in trichloroethylene) of about 6.0 hours as contrasted with 9.0 and 9.2 hours for disecondarybutyl peroxydicarbonate and di(2-ethylhexyl)peroxydicarbonate respectively.

The peroxydicarbonates represented by graphic formula I can be employed for the polymerization and copolymerization of ethylenically unsaturated monomers. Illustrative of such monomers include, but are not limited to, vinyl aromatic compounds such as styrene and p-chlorostyrene; esters of aliphatic alpha-methylene monocarboxylic acids such as methyl methacrylate, n-butyl acrylate, and ethyl acrylate; vinyl esters such as vinyl acetate; vinyl halides, e.g., vinyl chloride; vinyl ethers, e.g., vinyl methyl ethers; vinylidene halides such as vinylidene chloride; and alpha-ethylenically unsaturated hydrocarbons, such as ethylene and propylene, as well as for the cross-linking of unsaturated polyester resins. The polymerization of ethylenically unsaturated monomers can be performed as a suspension, emulsion, solution or bulk polymerization.

DETAILED DESCRIPTION OF THE INVENTION

The present invention relates to novel organic peroxydicarbonates represented by the following graphic formula:

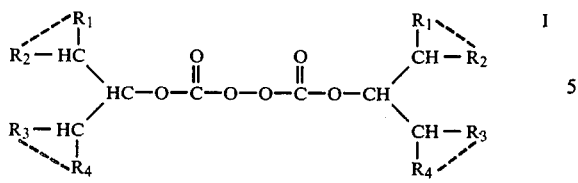 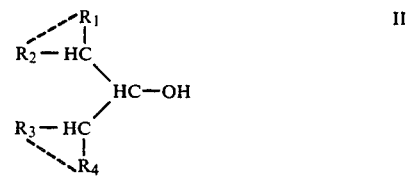

In the above formula I, $R_1$, $R_2$, $R_3$ and $R_4$ are each independently a $C_1$–$C_4$ alkyl, e.g., methyl, ethyl, n-propyl, isopropyl, n-butyl, isobutyl, secondary butyl and tertiary butyl groups or $R_1$ and $R_2$, and $R_3$ and $R_4$ can participate in a cycloalkyl group of from 3 to 6 carbon atoms (as shown by the broken lines connecting $R_1$ and $R_2$ and $R_3$ and $R_4$. When one of $R_1$ or $R_2$, or $R_3$ or $R_4$ is tertiary butyl, the other is other than tertiary butyl. Preferably $R_1$, $R_2$, $R_3$, and $R_4$ are each methyl. It is contemplated that $R_1$–$R_4$ can be the same or different. For example, $R_1$ and $R_4$ can be ethyl and $R_2$ and $R_3$ can be methyl. In another contemplated embodiment, $R_1$ and $R_2$ together participate to form a cyclohexyl group and $R_3$ and $R_4$ are each methyl. Illustrative of the peroxydicarbonates within the scope of graphic formula I are: di(2,4-dimethyl-3-pentyl)peroxydicarbonate, di(4-ethyl-2-methyl-3-hexyl)peroxydicarbonate, di(2,4-dimethyl-3-heptyl)peroxydicarbonate, di(1,1-dicyclohexylmethyl)peroxydicarbonate, di(2-cyclohexyl-4methyl-3-hexyl)peroxydicarbonate, di(2-cylopropyl-4-methyl-3-pentyl)peroxydicarbonate, di(2-cyclopentyl-4-methyl-3-pentyl)peroxydicarbonate, di(2,4-dicyclohexyl-3-pentyl)peroxydicarbonate, di(1,1-dicyclohexyl-3-methyl-2-butyl)peroxydicarbonate, di(3,5-dimethyl-4-hexyl)peroxydicarbonate, di(3-ethyl-5-methyl-4-hexyl)peroxydicarbonate, di(3,5-diethyl-4-hexyl)peroxydicarbonate, di(3,5-diethyl-4-heptyl)peroxydicarbonate, di(4,6-dimethyl-5-heptyl)peroxydicarbonate, di(4-ethyl-6-methyl-5-heptyl)peroxydicarbonate, di(4,6-dimethyl-5-nonyl)peroxydicarbonate, di(2,4,6-trimethyl-5-heptyl)peroxydicarbonate, di(2,4,6,8-tetramethyl-5-nonyl)peroxydicarbonate, di(2,2,3,5,6,6-hexamethyl-4-heptyl)peroxydicarbonate, di(2,2,3,6,6-pentamethyl-5-propyl-4-heptyl)peroxydicarbonate, and di-(2,2,3,6,6-pentamethyl-5-isobutyl-4-heptyl)peroxydicarbonate. The preferred peroxydicarbonate is di(2,4-dimethyl-3-pentyl)peroxydicarbonate.

The peroxydicarbonates of graphic formula I can be prepared from the chloroformate of the corresponding alcohol, e.g., 2,4-dimethyl-3-pentanol, using known techniques for the manufacture of symmetrical peroxydicarbonates. The aforesaid preparative technique involves the careful reaction of the aforesaid chloroformate with aqueous sodium peroxide at low temperatures, usually less than 20° C., e.g., 0° C.–10° C., and is described in U.S. Pat. No. 2,370,588 and in Volume 72, page 1254 et seq (1950) of the Journal of American Chemical Society.

The chloroformate of the precursor alcohol can be prepared by the reaction of the alcohol of the following graphic formula II with phosgene using well known phosgenation techniques.

The peroxydicarbonates of the present invention can be used to polymerize ethylenically unsaturated monomers or mixtures thereof. The commercially important monomer vinyl chloride is particularly suitable. Vinyl chloride can be homopolymerized or copolymerized with up to about 15 percent of another ethylenically unsaturated monomer. Examples of monomers which are copolymerizable with vinyl chloride include vinylidene chloride, ethylene, propylene and vinyl acetate. Polymerization of vinyl chloride is accomplished by contacting the vinyl chloride monomer or a mixture thereof with other monomers with an initiating amount of the peroxydicarbonate of the present invention under free-radical initiating conditions. Generally from about 0.003 to about 5, e.g., from 0.02 to 0.3, weight percent of the peroxydicarbonates of the present invention, based upon the total weight of monomer(s) polymerized, will be suitable for initiation of the polymerization. The precise amount of peroxydicarbonate used will vary with the monomer(s) to be polymerized and the polymerization temperatures. Typical levels of initiator required for such polymerizations are well known to those skilled in the art. The temperatures at which the polymerizable monomers are polymerized will typically range from about 35° C.–75° C.

The peroxydicarbonates of the present invention can also be used to cure unsaturated polyester resins. Unsaturated polyester resins which can be cured with peroxydicarbonates are well-known to those skilled in that art. Typically between about 0.05 and about 5, e.g., 0.2 to 2.5, parts by weight of the peroxydicarbonates of graphic formula I can be added to 100 parts by weight of the unsaturated polyester resin composition. The resultant mixture is heated at a temperature of from about 20° C. to about 150° C., e.g., 50° C. to 100° C., whereby the resin is cured.

The peroxydicarbonate of the present invention can be used in combination with the normally liquid peroxydicarbonates and other organic peroxides such as peresters, diacyl peroxides and azo compounds. For example, the peroxydicarbonates of the present invention can be used in combination with, for example diethyl peroxydicarbonate, diisopropyl peroxydicarbonate, di-n-propyl peroxydicarbonate, di-n-butyl peroxydicarbonate, di-secondary butyl peroxydicarbonate, di-tertiarybutyl peroxydicarbonate, di-2-ethylhexyl peroxydicarbonate, diacetyl peroxide, dilauryl peroxide, dibenzoyl peroxide, tertiarybutyl peroxypivalate, and azobisisobutyronitrile.

When used in combination with the normally liquid peroxydicarbonates, the mole ratio of the peroxydicarbonates of the present invention to that of the normally liquid peroxydicarbonate will typically range from about 0.01:1 to about 10:1, e.g., 1:1.

The present invention is more particularly described in the following Examples which are intended as illustrative only since numerous modifications and variations therein will be apparent to those skilled in the art.

EXAMPLE 1

Preparation of 2,4-Dimethyl-3-Pentyl Chloroformate

Into a one liter round bottom flask equipped with a phosgene inlet tube, a dry ice/2-propanol cooled condenser, a Teflon blade stirrer and a dropping funnel were added 200 milliliters (ml) of anhydrous ether. The flask was then cooled in dry ice/2-propanol bath and 200 ml of liquid phosgene (1.5 moles) were charged to the flask. A mixture of 100 grams (0.85 mole) of 2,4-dimethyl-3-pentanol, 67.2 grams (0.85 mole) of pyridine and 80 ml of anhydrous ether was added dropwise over a period of 4 hours through the dropping funnel to the pool of phosgene. When the addition was completed, the dry ice/2-propanol bath was removed and stirring was continued for several hours. Excess phosgene was removed by passing nitrogen through the reactor overnight. The phosgene-containing nitrogen gas stream removed from the reactor was forwarded to a packed column into the top of which was sprayed a solution of 15 weight percent sodium hydroxide which contained 0.8 weight percent pyridine. After degassing, the reaction mixture was filtered and the filtrate dried over anhydrous magnesium sulfate.

The ether solvent was evaporated and 136.3 grams (90 percent yield) of a light yellow liquid product was obtained. Identification of the product as 2,4-dimethyl-3-pentyl chloroformate was confirmed by Infrared (IR) and Nuclear Magnetic Resonance (NMR) spectroscopy. The assay was determined to be 99.9 percent based on chloroformate chlorine analysis. The acidity level of the product was nondetectable.

EXAMPLE 2

Preparation of Di(2,4-dimethyl-3-pentyl)peroxydicarbonate

Into a 500 ml slurry kettle equipped with a thermometer, a dropping funnel, a Teflon blade stirrer, and a bottom outlet connected to a Masterflex pump head were added a solution of 50 weight percent sodium hydroxide (12 grams, 0.16 mole) and 13 grams of distilled water. The caustic solution was cooled to 15° C. by an ice bath and 48% hydrogen peroxide (5.6 grams, 0.08 mole) was added slowly through the dropping funnel. A sodium peroxide slurry formed immediately. Tetrabutylammonium bromide (9.6 grams, 0.30 mole) dissolved in 50 ml of water was introduced into a 500 ml four-necked round bottom reactor flask equipped with a Teflon blade stirrer, a bottom stopcock, a vent, and a slurry inlet. 2,4-dimethyl-3-pentyl chloroformate (2.8 grams, 0.15 mole) was added to the reactor flask and the sodium peroxide slurry was transferred slowly to the reactor flask. The temperature within the reactor flask was maintained at about 10° C. by spraying ice water on the outside of the flask. On completing the addition of the sodium peroxide slurry, 20 grams of 2-propanol were added to the reaction mixture with stirring. The stirring was continued for 60 minutes. The organic layer was separated and washed three times with cold water (3×100 ml). The product was a brown viscous liquid which solidified when chilled by an ice bath. The solid was collected by filtration and washed several times with cold 2-propanol, thereby resulting in 17.5 grams of a white powder with a melting point of 46°–47° C. Identification of the product as di(2,4-dimethyl-3-pentyl)peroxydicarbonate was confirmed by IR and NMR spectroscopy. Iodometric titration of the product gave a percarbonate assay of 97.6%.

The half-life of di(2,4-dimethyl-3-pentyl)peroxydicarbonate at 50° C. was determined by maintaining separate aliquots of a 1.5M trichloroethylene solution of the peroxydicarbonate in 5 ml ampoules in a constant temperature bath maintained at 50±0.1° C. for various time intervals, and analyzing the amount of the peroxydicarbonate remaining in the ampoules after removal from the bath. The half-life was calculated to be 6.0 hours. The half-lives of disecondarybutylperoxydicarbonate and di(2-ethylhexyl)peroxydicarbonate were determined in the same manner and found to be 9.0 and 9.2 hours respectively.

EXAMPLE 3

Polymerization of Vinyl Acetate Monomer

Di(2,4-dimethyl-3-pentyl)peroxydicarbonate was used to polymerize vinyl acetate. For comparison, vinyl acetate was also polymerized using di(2-ethylhexyl)peroxydicarbonate. The polymerizations were performed in the following manner:

Vinyl acetate (50 grams), 0.05 mole percent of the peroxydicarbonate initiator, basis the vinyl acetate monomer, and 100 grams of a 0.1 weight percent aqueous solution of Methocel E-50 suspending agent were charged to 28 ounce polymerization bottles which were chilled by an ice bath. The atmosphere inside the bottles was removed by passing argon through the mixture for three minutes. The bottles were then capped, sealed and secured in safety cages. The cages and bottles were placed in a constant temperature water bath maintained at 40° C. and the bottles tumbled at a rate of 30 revolutions per minute for four hours.

One bottle was removed from the water bath at the end of each hour. This bottle was opened immediately and the contents poured into a two-liter beaker containing about 1500 milliliters of hot water (about 50°–60° C.). The resulting aqueous suspension was then heated to boiling to remove the unreacted vinyl acetate monomer. The precipitated polymer was collected, washed with distilled water and dried in a vacuum oven at room temperature for at least 24 hours.

The intrinsic viscosity (in toluene, 25° C.) of each dried product was determined and the molecular weight of each polymer product was calculated from the intrinsic viscosity according to the Mark-Houwink Equation. Results obtained are tabulated in Table I.

TABLE I

Suspension Polymerization of Vinyl Acetate at 40° C.

| Peroxydi-carbonate | Amt. (Mole %) | Poly(vinyl acetate) % Conversion (Molecular Weight, $10^5$) | | | |
|---|---|---|---|---|---|
| | | 1 hr. | 2 hrs. | 3 hrs. | 4 hrs. |
| 1. Example 2[a] | .05 | 38 (6.0) | 81 (8.8) | 84 (9.4) | 86 (10.0) |
| 2. EHP[b] | .05 | 26 (3.3) | 57 (4.5) | 81 (6.0) | 85 (5.6) |

[a] Di(2,4-dimethyl-3-pentyl) peroxydicarbonate
[b] Di(2-ethylhexyl) peroxydicarbonate The data of Table I show that the rate of conversion of vinyl acetate to polyvinylacetate is significantly greater for di(2,4-dimethyl-3-pentyl)peroxydicarbonate than the rate obtained with di(2-ethylhexyl)peroxydicarbonate. After two hours, 81% of the vinyl acetate had been polymerized to a polymer of 880,000 molecular weight using the peroxydicarbonate of the present invention whereas only 57% of the vinyl acetate had been converted to a polymer having a molecular weight of 450,000 after two hours utilizing di(2-ethylhexyl)-peroxydicarbonate. This data confirms the half-life data reported in Example II and demonstrates that the peroxydicarbonate of the present invention is significantly more active than the normally liquid peroxydicarbonates commercially available. Use of the peroxydicarbonates of the present invention permits equivalent monomer conversions in a shorter time, thereby allowing for less batch times and hence more production in a given time period.

Although the present invention has been described with reference to specific details of certain embodiments thereof, it is not intended that such details be regarded as limitations upon the scope of the invention except as and to the extent that they are included in the accompanying claims.

What is claimed is:

1. An organic peroxydicarbonate of the graphic formula:

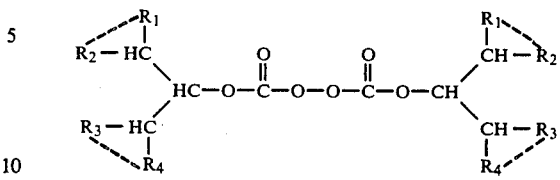

wherein $R_1$, $R_2$, $R_3$ and $R_4$ are each independently a $C_1$–$C_4$ alkyl, provided that not more than one of $R_1$ and $R_2$, and not more than one of $R_3$ and $R_4$ is tertiarybutyl, or $R_1$ and $R_2$, and $R_3$ and $R_4$ participate independently in a cycloalkyl group of from 3 to 6 carbon atoms.

2. An organic peroxydicarbonate in accordance with claim 1 wherein $R_1$, $R_2$, $R_3$ and $R_4$ are each selected from the group consisting of methyl and ethyl.

3. Di(2,4-dimethyl-3-pentyl)peroxydicarbonate.